United States Patent [19]

Ciganek

[11] Patent Number: 4,485,109

[45] Date of Patent: Nov. 27, 1984

[54] 4-ARYL-4-PIPERIDINECARBINOLS

[75] Inventor: Engelbert Ciganek, Kennett Square, Pa.

[73] Assignee: E. I. Du Pont de Nemours and Company, Wilmington, Del.

[21] Appl. No.: 468,040

[22] Filed: Feb. 25, 1983

Related U.S. Application Data

[63] Continuation-in-part of Ser. No. 376,229, May 7, 1982, abandoned.

[51] Int. Cl.³ ................ A61K 31/445; C07D 211/22; C07D 409/04; C07D 403/04; C07D 221/04; C07D 215/14; C07D 211/26

[52] U.S. Cl. .................................... 424/267; 424/258; 546/240; 546/232; 546/205; 546/206; 546/208; 546/193; 546/194; 546/212; 546/213; 546/164; 546/112

[58] Field of Search ............... 546/240, 205, 206, 208, 546/232, 193, 194, 212, 213, 164, 112; 424/267, 258

[56] References Cited

U.S. PATENT DOCUMENTS

| | | | |
|---|---|---|---|
| 2,739,968 | 3/1956 | Sperber et al. | 546/248 |
| 2,832,786 | 4/1958 | Tilford et al. | 260/294.7 |
| 3,080,372 | 3/1963 | Janssen | 546/240 |
| 3,108,211 | 10/1963 | Stern et al. | 546/240 |
| 3,824,242 | 7/1974 | Levine et al. | 260/295 R |
| 3,912,743 | 10/1975 | Christensen et al. | 260/293.58 |
| 4,228,288 | 10/1980 | Zimmerman | 546/339 |
| 4,236,009 | 11/1980 | Zimmerman et al. | 546/112 |
| 4,241,071 | 12/1980 | Martin et al. | 546/240 |
| 4,277,608 | 7/1981 | Zimmerman et al. | 546/339 |

FOREIGN PATENT DOCUMENTS

| | | |
|---|---|---|
| 1079734 | 6/1980 | Canada . |
| 0013078 | 7/1980 | European Pat. Off. . |
| 47-18878 | 9/1972 | Japan ..................... 546/240 |
| 841120 | 7/1960 | United Kingdom . |
| 888657 | 1/1962 | United Kingdom . |

OTHER PUBLICATIONS

M. A. Iorio et al., Chimica Therapeutica, (1971), vol. 6, (5), pp. 391–396.
Kägi et al., Helvetica Chimica Acta, 32, 2489–2507, (1949); Translation.
Lewis et al., J. Chem. Soc., (C), 1970, 1074–1075.
Martin et al., Tetrahedron Letters, 3925–3928, (1977).
Evans et al., J. Am. Chem. Soc., 102, 5955–6, (1980).
M. A. Iorio et al., Tetrahedron, vol. 27, (1971), pp. 4983–4989.

Primary Examiner—Norma S. Milestone

[57] ABSTRACT

4-Aryl-4-piperidinecarbinols, for example,

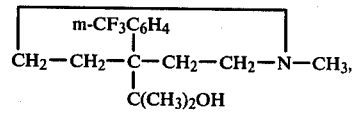

useful as antidepressants and, in some cases, as anorectic agents.

15 Claims, No Drawings

4-ARYL-4-PIPERIDINECARBINOLS

CROSS-REFERENCE TO RELATED APPLICATION

This is a continuation-in-part of patent application Ser. No. 376,229 filed May 7, 1982, now abandoned.

DESCRIPTION

TECHNICAL FIELD

This invention relates to 4-aryl-4-piperidinecarbinols which are useful as antidepressants and, in some cases, an anorectic agents.

BACKGROUND

Mental illness encompasses both psychoses and neuroses. Symptoms requiring treatment include depression, anxiety, agitation, and hallucinations. Among the drugs used particularly for treatment of both reactive and endogenous depressions are monoamine oxidase (MAO) inhibitors, such as iproniazide, tranylcypromine, nialamide, phenelzine, and pargyline, and the non-MAO-inhibiting tricyclic aromatic dibenzazepines, such as imipramine, and dibenzocycloheptanes such as amitriptyline.

All of these drugs have adverse side effects that limit their usefulness. MAO inhibitors may benefit milder forms of depression, but the risk of serious toxic effects is a strong argument against their use. They may cause liver damage and acute hypertension, especially if given in conjunction with cheese, bananas, or other amine-containing foods. The MAO inhibitors may also cause tremors, insomnia, hyperhydrosis, agitation, hypermanic behaviour, confusion, hallucinations, convulsions and orthostatic hypotension. They frequently cause dizziness, vertigo, headache, inhibition of ejaculation, difficulty in urination, weakness, fatigue, dry mouth, constipation and blurred vision.

Imipramine may cause blurred vision, dryness of mouth, constipation, urinary retention, orthostatic hypotension, respiration depression, myocardial infarction, and congestive heart failure. Similar difficulties are experienced with amitriptyline.

There is a continuing need for psychotherapeutic agents that have fewer side effects than the drugs in use today; also for psychotherapeutic agents that have different modes of action than presently used agents, since none of these is completely effective.

British Patent Specification No. 888,657 and Canadian Pat. No. 1,079,734 disclose piperidinecarbinols, useful as analgesics and cough suppressants, of the formula

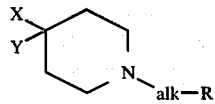

wherein
X is phenyl;
Y is hydroxymethyl, 1-hydroxymethyl or 1-hydroxypropyl;
alk is alkylene of up to six carbon atoms; and
R is an oxygen- or nitrogen-containing heterocyclic group, tetrahydrofurfuryloxyethyl, aryl, aryloxy, aralkoxy, alkoxy of up to six carbon atoms or alkoxy substituted by hydroxy, ethoxy or phenoxy.

Compounds of such structure wherein Y is alkanoyl and the other substituents are similarly defined are also known from British Patent Specification No. 841,120.

Kägi et al., *Helvetica Chimica Acta*, Vol. XXXII, 2489 (1949) disclose the synthesis of various analgesics; intermediate compounds of the formula

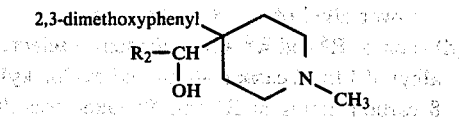

wherein
$R_2$ is $CH_3$ or $n$-$C_3H_7$ are disclosed.

Lewis et al., *J. Chem. Soc. C.*, 1970, 1074, disclose compounds of the formula

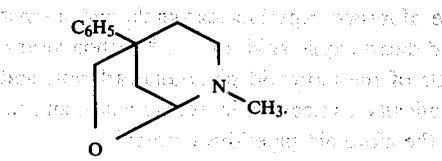

DISCLOSURE OF INVENTION

For further comprehension of the invention and of the objects and advantages thereof, reference may be made to the following description and to the appended claims in which the various novel features of the invention are more particularly set forth.

The invention resides in 4-aryl-4-piperidinecarbinols of the formula

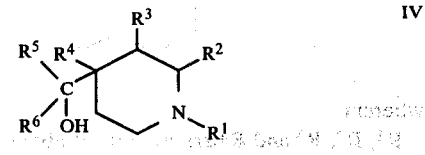

wherein
(a) $R^1$ is H, alkyl of 1 to 12 carbon atoms, cycloalkyl of 3 to 8 carbon atoms or benzyl;
(b) each of $R^2$ and $R^3$ is independently selected from H and lower alkyl of 1 to 4 carbon atoms; $R^1$ and $R^2$ taken together is a branched or unbranched alkylene bridge wherein the bridge is of 3 or 4 carbon atoms; or $R^2$ and $R^3$ taken together is a branched or unbranched alkylene bridge wherein the bridge is of 3 to 6 carbon atoms;
(c) $R^4$ is
  (1) phenyl or 2-naphthyl or phenyl or 2-naphthyl substituted with one or two substituents, the same or different, selected from F, Cl, alkyl, perfluoroalkyl, alkoxy, aryloxy, alkylthio, arylthio, perfluoroalkoxy, perfluoroalkylthio and dialkylamino, said alkyl and alkoxy moieties being of 1 to 12 carbon atoms and said aryl moieties being of 6 to 12 carbon atoms;
  (2) 2-, 3- or 4-biphenylyl or 2-, 3- or 4-biphenylyl wherein either or both aromatic moieties is substituted with one or two substituents, the same or different, selected from F, Cl, alkyl, perfluoroalkyl, alkoxy, aryloxy, alkylthio, arylthio, perfluoroalkoxy, perfluoroalkylthio and dialkylamino, said alkyl and alkoxy moieties being of 1 to 12 carbon atoms and said aryl moieties being of 6 to 12 carbon atoms;

(3) 2-pyrrolyl or 2-pyrrolyl substituted with one to three lower alkyl groups of 1 to 4 carbon atoms;

(4) 2-, 3-, or 4-pyridyl; or (5) 2-thienyl substituted in the 5-position with lower alkyl of 1 to 4 carbon atoms;

(d) each of $R^5$ and $R^6$ is independently selected from alkyl of 1 to 12 carbon atoms and cycloalkyl of 3 to 8 carbon atoms or $R^5$ and $R^6$ taken together is a branched or unbranched alkylene bridge wherein the bridge is of 3 to 11 carbon atoms, provided, however, when $R^1$, $R^5$ and $R^6$ are methyl and $R^2$ and $R^3$ are H, then $R^4$ is not p-t-butylphenyl or 2'-biphenylyl. The invention herein also resides in esters of the aforesaid piperidinecarbinols and aliphatic mono- and dicarboxylic acids of 1 to 8 carbon atoms; in amine salts of the aforesaid piperidinecarbinols and pharmaceutically compatible inorganic acids; and in N-oxides of the aforesaid piperidinecarbinols.

The 4-aryl-4-piperidinecarbinols of this invention can be prepared by a series of reactions carried out in sequence as follows:

(1) $R^4Br$ is lithiated with n-butyllithium to produce $R^4Li$ which is then reacted with the piperidinone of the formula:

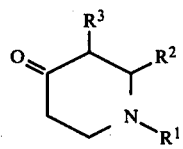

wherein
$R^1$, $R^2$, $R^3$ and $R^4$ are as defined above, to produce

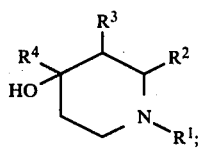

I (2) I is dehydrated to the mixed olefins

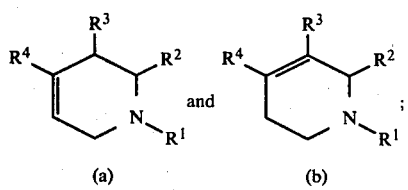

II (3) II is lithiated with n-butyllithium and then reacted with the ketone $R^5COR^6$ wherein $R^5$ and $R^6$ are as defined above, to produce the oxaazabicyclooctane

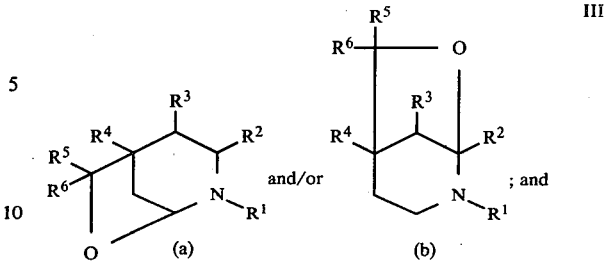

III (4) III is reduced to produce IV.

Alternatively, II after lithiation can be reacted with the ester $R^5COOR^7$ wherein $R_5$ is as defined above and $R^7$ is lower alkyl of 1 to 4 carbon atoms, to produce the ketone

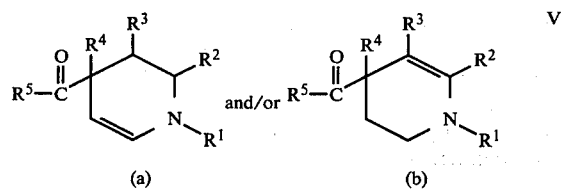

V which can then be reacted with $R^6Li$ or $R^6MgX$ wherein $R^6$ is as defined above and X is Cl, Br or I, to produce III. As is apparent, this alternate method cannot be used if $R^5$ and $R^6$ taken together in IV is alkylene.

Following are more specific details of the reactions outlined above. It is to be understood that the above outline is not intended to be limiting.

(1) Preparation of I

Lithiation of $R^4Br$ can be carried out at $-100°$ C. to $50°$ C. in an ethereal solvent, for example, diethyl ether or tetrahydrofuran. Known commonly used lithiating agents include, for example, n-butyllithium, methyllithium and sec- and tert-butyllithium. As known in the art, a magnesium (Grignard) reagent may be used instead of the alkyl lithium compound, in which event the intermediate produced is an organomagnesium compound. Also as known in the art, for example, as disclosed by Gschwend and Rodriguez, Organic Reactions, Volume 26, some compounds $R^4H$ wherein $R^4$ is as defined above can be lithiated directly rather than via the intermediate $R^4Br$. Tetramethylethylenediamine may be employed in conjunction with the alkyl lithium compound. Such directly-lithiated compounds include the alkoxybenzenes, wherein lithiation occurs ortho to the alkoxy substituent, and pyrrole and 5-alkylthiophenes, wherein lithiation occurs at the 2-positions.

In the second step of the preparation of I, the organolithium or organomagnesium compound is reacted with the aforesaid piperidinone either neat or in an ethereal solvent, for example, diethyl ether or tetrahydrofuran, at $-70°$ C. to $50°$ C.

(2) Preparation of II

The dehydration of I to II can be carried out in the presence of a catalyst, such as hydrochloric acid, hydrobromic acid, methanesulfonic acid/phosphorus pentoxide, trifluoroacetic acid or an arylsulfonic acid, either in a solvent, such as an aromatic hydrocarbon, or in the absence of a solvent. Depending on the nature of the substituents $R^1$, $R^2$, $R^3$ and $R^4$, the dehydration can be carried out at an appropriate temperature within the range 0° C. to 200° C. After dehydration the acid catalyst is neutralized to convert the amine salt to the free amine II.

(3) Preparation of III

Compound II can be metalated as described above in connection with the preparation of I. Lithiation can be carried out at −70° C. to 70° C., preferably at −10° C. to −20° C., in the absence of both oxygen and water. The metal salt, in solution, thus produced can be reacted with the aforesaid ketone $R^5COR^6$ in an ethereal solvent, for example, diethyl ether or tetrahydrofuran, at −100° C. to 50° C. Upon hydrolysis of the resultant lithium or magnesium salt, III is obtained.

(4) Preparation of IV

Reduction of III provides IV. The reduction can be effected by means of borohydride reagents, such as sodium borohydride in an alcohol or sodium cyanoborohydride in an alcohol/acetic acid mixture, or by means of catalytic hydrogenation, for example, using a palladium catalyst, in an acetic acid or alcohol solvent in the presence of a mineral acid.

In the aforesaid alternative procedure, the metalated II, in solution, can be reacted with the ester $R^5COOR^7$ to produce V which is reacted with $R^6Li$ or $R^6MgX$ in an ethereal solvent at −20° C. to 50° C. Upon hydrolysis of the resultant lithium or magnesium salt, III is obtained.

In any of the aforesaid procedures wherein are present compounds having the piperidine moiety, the N-substituent can be benzyl instead of $R^1$, in which case the ultimate product is IV except that the N-substituent is benzyl instead of $R^1$. The N-benzylated product is a valuable intermediate and can be converted by catalytic hydrogenolysis, using a palladium catalyst in an acetic acid solvent, to the secondary amine, that is, IV wherein $R^1$ is H. The secondary amine can be alkylated by means of the appropriate alkyl or cycloalkyl halide to produce IV wherein $R^1$ is alkyl of 1 to 12 carbon atoms or cycloalkyl of 3 to 8 carbon atoms. Some of the $R^1$ groups can be introduced by an alternate method in which the secondary amine is first acylated with an acyl chloride, the acyl group of which corresponds, when reduced, to the desired $R^1$ group. The amide which is produced by acylation can be reduced with a hydride reducing agent, such as $BH_3$ or $LiAlH_4$, to provide the desired amine IV.

Suitable salts with pharmacologically acceptable acids, such as hydrochloric, sulfuric, phosphoric, and maleic acids, may be prepared from all free bases IV. Such salts may be preferable when the free bases are oils. Salts of bases IV may also be more stable to storage, and may be better absorbed orally, than the free bases.

In the following examples, all temperatures are in degrees Celsius. Table 1 summarizes the compounds prepared in the examples. In the table "Me" is $CH_3$, "Et" is $C_2H_5$, "Ph" is $C_6H_5$, "PhCH$_2$" is benzyl and "Cp" is cyclopentyl.

TABLE 1

| Ex. No. | $R^1$ | $R^2$ | $R^3$ | $R^4$ | $R^5$ | $R^6$ |
|---|---|---|---|---|---|---|
| 1 | Me | H | H | Ph | Me | Me |
| 2 | Me | H | H | m-CF$_3$C$_6$H$_4$ | Me | Me |
| 3 | Me | H | H | 2,3-(MeO)$_2$C$_6$H$_3$ | —(CH$_2$)$_4$— | |
| 4 | Me | H | H | m-FC$_6$H$_4$ | Me | Me |
| 5 | Me | H | H | p-FC$_6$H$_4$ | Me | Me |
| 6 | Me | H | H | m-ClC$_6$H$_4$ | Me | Me |
| 7 | Me | H | H | p-ClC$_6$H$_4$ | Me | Me |
| 8 | Me | H | H | m-ClC$_6$H$_4$ | Et | Et |
| 9 | Me | H | H | o-MeC$_6$H$_4$ | Me | Me |
| 10 | Me | H | H | m-MeC$_6$H$_4$ | Me | Me |
| 11 | Me | H | H | p-MeC$_6$H$_4$ | Me | Me |
| 12 | Me | H | H | 3,5-Me$_2$C$_6$H$_3$ | Me | Me |
| 13 | Me | H | H | 3,4-Me$_2$C$_6$H$_3$ | Me | Me |
| 14 | H | H | H | m-MeOC$_6$H$_4$ | Me | Me |
| 15 | Me | H | H | o-MeOC$_6$H$_4$ | Me | Me |
| 16 | Me | H | H | m-MeOC$_6$H$_4$ | Me | Me |
| 17 | Me | H | H | m-MeOC$_6$H$_4$ | Me | Et |
| 18 | Me | H | H | m-MeOC$_6$H$_4$ | Et | Et |
| 19 | Me | H | H | p-MeOC$_6$H$_4$ | Me | Me |
| 20 | Me | H | H | 2,3-(MeO)$_2$C$_6$H$_3$ | Me | Me |
| 21 | Me | H | H | p-MeSC$_6$H$_4$ | Me | Me |
| 22 | Me | H | H | m-MeOC$_6$H$_4$ | —(CH$_2$)$_3$— | |
| 23 | Me | H | H | 2,3-(MeO)$_2$C$_6$H$_3$ | —(CH$_2$)$_5$— | |
| 24 | Me | H | H | 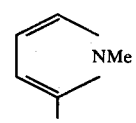 | Me | Me |
| 25 | Me | H | H | 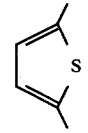 | Me | Me |

TABLE 1-continued

| Ex. No. | R¹ | R² | R³ | R⁴ | R⁵ | R⁶ |
|---|---|---|---|---|---|---|
| 26 | Me | H | H | (3,4-dihydro-2H-pyridinyl structure) | Me | Me |
| 27 | Me | H | H | m-MeOC$_6$H$_4$ | —(CH$_2$)$_6$— | |
| 28 | Me | H | H | m-MeOC$_6$H$_4$ | —(CH$_2$)$_7$— | |
| 29 | Me | H | H | 2,5-(MeO)$_2$C$_6$H$_3$ | Me | Me |
| 30 | Me | H | H | m-CF$_3$C$_6$H$_4$ | —(CH$_2$)$_4$— | |
| 31 | Me | H | H | m-CF$_3$C$_6$H$_4$ | Me | Et |
| 32 | Me | H | H | p-PhOC$_6$H$_4$ | Me | Me |
| 33 | Me | H | H | p-Me$_2$NC$_6$H$_4$ | Me | Me |
| 34 | Me | H | H | m-MeOC$_6$H$_4$ | —(CH$_2$)$_4$— | |
| 35 | Me | H | H | m-MeOC$_6$H$_4$ | —(CH$_2$)$_5$— | |
| 36 | Me | H | H | m-PhC$_6$H$_4$ | Me | Me |
| 37 | PhCH$_2$ | H | H | 2,3-(MeO)$_2$C$_6$H$_3$ | Me | Me |
| 38 | PhCH$_2$ | H | H | 2,3-(MeO)$_2$C$_6$H$_3$ | —(CH$_2$)$_4$— | |
| 39 | Me | H | H | 6'-methoxy-2'-naphthyl | Me | Me |
| 40 | Me | H | H | m-EtOC$_6$H$_4$ | Me | Me |
| 41 | Et | H | H | m-CF$_3$C$_6$H$_4$ | Me | Me |
| 42 | Me | H | H | 4'-biphenylyl | Me | Me |
| 43 | Me | H | CH$_3$ | m-CH$_3$OC$_6$H$_4$ | Me | Me |
| 44 | Me | CH$_3$ | H | m-CH$_3$C$_6$H$_4$ | Me | Me |
| 45 | —(CH$_2$)$_3$— | | H | m-CF$_3$C$_6$H$_4$ | Me | Me |
| 46* | Me | H | H | m-CF$_3$C$_6$H$_4$ | —CH$_2$CH$_2$CH(CH$_3$)CH$_2$—⁺ | |
| 47** | Me | H | H | m-CF$_3$C$_6$H$_4$ | —CH$_2$CH$_2$CH(CH$_3$)CH$_2$—± | |

*dl-mixture of cis and trans isomers.
**l-mixture of cis and trans isomers.
⁺epimers at this position.
±single configuration at this position.

Table 1A includes additional preferred embodiments of the invention; these embodiments, however, are not exemplified herein.

TABLE 1A

| Ex. No. | R¹ | R² | R³ | R⁴ | R⁵ | R⁶ |
|---|---|---|---|---|---|---|
| 1 | Me | H | H | m-CF$_3$C$_6$H$_4$ | —(CH$_2$)$_2$CHCH$_2$—<br>\|<br>Me | |
| 2 | Me | H | H | m-CF$_3$C$_6$H$_4$ | —CH$_2$CHCH$_2$—<br>\|<br>Me | |
| 3 | Me | H | H | m-CF$_3$OC$_6$H$_4$ | Me | Me |
| 4 | Me | H | H | m-CF$_3$SC$_6$H$_4$ | Me | Me |
| 5 | Cp | H | H | m-CF$_3$C$_6$H$_4$ | Me | Me |
| 6 | Me | —(CH$_2$)$_3$— | | m-CF$_3$C$_6$H$_4$ | Me | Me |
| 7 | Me | —(CH$_2$)$_4$— | | m-CF$_3$C$_6$H$_4$ | Me | Me |
| 8 | Me | —(CH$_2$)$_6$— | | m-CF$_3$C$_6$H$_4$ | Me | Me |
| 9 | —(CH$_2$)$_4$— | | H | m-CF$_3$C$_6$H$_4$ | Me | Me |
| 10 | Me | H | H | 2-pyridyl | Me | Me |
| 11 | Me | H | H | 4-pyridyl | Me | Me |
| 12 | Me | H | H | m-C$_2$F$_5$C$_6$H$_4$ | Me | Me |
| 13 | Me | H | H | m-PhSC$_6$H$_4$ | Me | Me |

EXAMPLE 1

4-Phenyl-α,α,1-trimethyl-4-piperidinemethanol n-Butyllithium (15 ml of 1.5M solution in hexane) was added under nitrogen to a solution of 4.7 g of commercially available 1-methyl-4-phenyl-1,2,3,6-tetrahydropyridine (II: R¹=Me; R², R³=H; R⁴=phenyl) in 50 mL of tetrahydrofuran, kept at −10°. The deep red solution was stirred at −10° for 15 min and then transferred in a slow stream into a stirred mixture of 15 mL of acetone and 25 mL of tetrahydrofuran and kept at −70°. Excess 10% hydrochloric acid was added after stirring at −70° for 5 min; the mixture was allowed to come to room temperature, and then washed with toluene. The aqueous layer was made basic with sodium hydroxide and extracted with methylene chloride. Removal of the solvent from the dried solution and short-path distillation of the residue (90°–135° bath temperature, 5×10$^{-4}$ mm Hg [0.07 Pa]) gave 2.79 g of 5-phenyl-2,6,6-trimethyl-7-oxa-2-azabicyclo[3.2.1]octane (III: R¹, R⁵, R⁶=Me; R², R³=H, R⁴=phenyl) as an oil of ca. 85% purity.

A solution of 1.47 g of the above product III in a mixture of 10 mL of methanol and 2 mL of acetic acid was cooled with ice and treated with 0.76 g of sodium cyanoborohydride. The mixture was stirred at room temperature for 2 h, and the excess borohydride was decomposed by addition, with ice cooling, of 8 mL of conc hydrochloric acid. After stirring at room temperature for 0.5 h the mixture was made basic with aqueous sodium hydroxide solution and extracted with methylene chloride. Removal of the solvent from the dried solution and crystallization of the residue from ethyl acetate gave 0.98 g of 4-phenyl-α,α,1-trimethyl-4-piperidinemethanol, m.p. 146°–147°. NMR (220 MHz in CDCl$_3$): τ 2.7–2.8 (m, 5H); 7.0–8.2 (m, 9H); 8.0 (s, 3H) and 8.9 (s, 6H). Anal. Calcd. for C$_{15}$H$_{23}$NO: C, 77.21; N, 9.94; N, 6.00. Found: C, 77.12; H, 9.89; N, 6.00.

EXAMPLE 2

4-(3'-Trifluoromethylphenyl)-α,α,1-trimethyl-4-piperidinemethanol and its Hydrochloride A 1.5M solution of n-butyllithium in hexane (150 mL) was added under nitrogen at −70° to a stirred solution of 50 mg of 3-bromobenzotrifluoride in 300 mL of tetrahydrofuran. The mixture was stirred at −70° for 15 min and then allowed to warm to −20°. A solution of 30 g of freshly distilled 1-methyl-4-piperidone in 50 mL of tetrahydrofuran was added slowly, keeping the temperature at −20°. The mixture was then stirred at 0° for 0.5 h, and at room temperature for 3 h. Water and methylene chloride were added and the aqueous layer was extracted several times with methylene chloride. Removal of the solvent from the combined and dried methylene chloride solutions, and short-path distillation of the residue (110°–130° bath temp., 5×10⁻⁴ mm Hg [0.07 Pa]) gave 41.6 g of 1-methyl-4-(3′-trifluoromethylphenyl)-4-piperidinol (I: $R^1$=Me; $R^2$, $R^3$=H; $R^4$=m-trifluoromethylphenyl) as a solid.

A mixture of 28.1 g of this product I and 100 mL of trifluoroacetic acid was heated under reflux for 24 h. The excess acid was removed under vacuum, the residue was dissolved in methylene chloride and the solution was made basic with 10% aqueous sodium carbonate solution. Removal of the solvent from the dried organic phase and short-path distillation of the residue gave 24.06 g of 1-methyl-4-(3′-trifluoromethylphenyl)-1,2,3,6-tetrahydropyridine (IIa: $R^1$=Me; $R^2$, $R^3$=H; $R^4$=m-trifluoromethylphenyl).

To a solution of this product IIa in 150 mL of tetrahydrofuran was added, at −10°, 80 mL of a 1.5M solution of n-butyllithium in hexane. The red solution was stirred at −10° for 15 min and then transferred in a slow stream into a stirred mixture of 60 mL of acetone and 60 mL of tetrahydrofuran, kept at −20°. The mixture was allowed to come to 10° and was then treated with 10% aqueous sodium chloride solution. The layers were separated and the aqueous phase was extracted repeatedly with methylene chloride. Removal of the solvent from the combined, dried organic phases gave 34.35 g of crude 5-(3′-trifluoromethylphenyl)-2,6,6-trimethyl-7-oxa-2-azabicyclo[3.2.1]octane (III: $R^1$, $R^5$, $R^6$=Me; $R^2$, $R^3$=H; $R^4$=m-trifluoromethylphenyl). This product III was dissolved in a mixture of 150 mL of methanol and 25 mL of acetic acid and the solution, ice cooled, was treated with 9 g of sodium cyanoborohydride. Concentrated hydrochloric acid (50 mL) was added after stirring at room temperature for 2 h, and after a further 0.5 h, the mixture was made basic with aqueous sodium hydroxide solution and extracted with methylene chloride. Removal of the solvent from the dried organic phases gave 31.74 g of a product which was partitioned between dilute hydrochloric acid and ether/toluene. Rebasification of the aqueous phase followed by methylene chloride extraction gave 27.40 g of product. Short-path distillation (to 210° bath temp., 10⁻³ mm Hg [0.1 Pa]) and crystallization of the distillate from cyclohexane gave 7.59 g of 4-(3′-trifluoromethylphenyl)-α,α,1-trimethyl-4-piperidinemethanol, m.p. 111°–112°. NMR (90 MHz in CDCl₃): τ2.3–2.6 (m, 4H); 7.1–8.3 (m, 9H); 7.8 (s, 3H) and 8.8 (s, 6H); ¹⁹F NMR (in CDCl₃): singlet at −63.02 ppm from CFCl₃. The hydrochloride (referred to in Table 2 as Example 2A) had a m.p. of 240°–241° after crystallization from isopropyl alcohol. Anal. Calcd. for C₁₆H₂₃ClF₃NO: C, 56.89; H, 6.86; N, 4.15. Found: C, 57.03; H, 6.78; N, 4.07.

EXAMPLE 3

1-[1′-Methyl-4′-(2″,3″-dimethoxyphenyl)-4′-piperidinyl]cyclopentanol

A solution of 138 g of veratrole in 400 mL of dry tetrahydrofuran was cooled in a dry ice/acetone bath and treated with 500 mL of a 1.6M solution of n-butyllithium at such a rate that the temperature of the reaction mixture remained at 0°. After the addition was completed the reaction mixture was stirred at room temperature for 3 h. At the end of this period the resulting white slurry was cooled in a dry ice/acetone bath and 90.4 g of 1-methyl-4-piperidone was added at such a rate that the temperature of the reaction mixture remained below −10°. After the addition was completed the reaction mixture was stirred at 0° for 2 h, quenched with 400 mL of water and diluted with 400 mL of ether. The organic layer was separated and the aqueous layer was extracted with methylene chloride (3×400 mL). The combined organic layers were dried (K₂CO₃) and concentrated under reduced pressure to afford 270.9 g of an oil. This oil was heated under reduced pressure to remove all the material boiling below 150°/0.025 mm Hg (3.3 Pa). The residue (97.55 g) contained the desired 4-(2′,3′-dimethoxyphenyl)-1-methyl-4-piperidinol (I: $R^1$=Me, $R^2$, $R^3$=H; $R^4$=2,3-dimethoxyphenyl) and was used without further purification in the next step.

A solution of 79.49 g of this product I in 238 mL of conc hydrochloric acid was heated to 65° for 3 h. At the end of this period the reaction mixture was cooled to room temperature, made basic with 20% aqueous sodium hydroxide solution, and extracted with portions (3×200 mL) of methylene chloride; the combined organic layers were dried (K₂CO₃) and concentrated under reduced pressure. The product thus obtained was distilled under reduced pressure to yield 4-(2′,3′-dimethoxyphenyl)-1-methyl-1,2,3,6-tetrahydropyridine (IIa: $R^1$=Me; $R^2$, $R^3$=H; $R^4$=2,3-dimethoxyphenyl) as a colorless oil, bp 100°–120°/0.05 mm Hg (7 Pa), 73.56 g (84.8% yield).

A solution of 4.7 g of this product IIa in 50 mL of tetrahydrofuran was treated with n-butyllithium as described in Example 1 and the solution of the lithium salt was added to a mixture of 20 mL of cyclopentanone and 30 mL of tetrahydrofuran at −70°. Isolation as described in Example 1 and crystallization of the crude product from ethyl acetate gave 3.29 g of 2′-methyl-5′-(2″,3″-dimethoxyphenyl)spiro[cyclopentane-1,6′-[7]-oxa[2]azabicyclo[3.2.1]octane] (III: $R^1$=Me; $R^2$, $R^3$=H; $R^4$=2,3-dimethoxyphenyl; $R^5$, $R^6$=(CH₂)₄), m.p. 110°. Anal. Calcd. for C₁₉H₂₇NO₃: C, 71.89; H, 8.57; N, 4.41. Found: C, 72.24; H, 8.45; N, 4.52.

Reduction of the immediately preceding product with sodium cyanoborohydride as described in Example 1 gave 1-[1′-methyl-4′-(2″,3″-dimethoxyphenyl)-4′-piperidinyl]cyclopentanol, m.p. 114°–115°. Anal. Calcd. for C₁₉H₂₉NO₃: C, 71.44; H, 9.15; N, 4.38. Found: C, 71.49; H, 9.01; N, 4.41.

EXAMPLE 4

4-(3′-Fluorophenyl)-α,α,1-trimethyl-4-piperidinemethanol 4-(3′-Fluorophenyl)-α,α,1-trimethyl-4-piperidinemethanol was prepared from 3-bromofluorobenzene by the procedure described in Example 2; m.p. 158°–159°; NMR (in CDCl₃): τ2.5–3.2 (m, 4H); 7.2–8.3 (m, 12H) and 8.8 (s, 6H); ¹⁹F NMR (in CDCl₃): singlet (after H-decoupling) at −117.4 ppm from CFCl₃. Anal. Calcd. for C₁₅H₂₂FNO: C, 71.68; H, 8.82; N, 5.57. Found: C, 71.68; H, 8.77; N, 5.69.

EXAMPLE 5

4-(4′-Fluorophenyl)-α,α,1-trimethyl-4-piperidinemethanol 4-(4′-Fluorophenyl)-α,α,1-trimethyl-4-piperidinemethanol was prepared from 4-bromofluorobenzene by the procedure described in Example 2; m.p. 165°–166°; NMR (in CDCl$_3$): τ2.6–3.1 (m, 4H); 7.2–8.7 (m, 12H) and 8.9 (s, 6H); $^{19}$F NMR (in CDCl$_3$): singlet (after H-decoupling) at −117.6 ppm from CFCl$_3$. Anal. Calcd. for C$_{15}$H$_{22}$FNO: C, 71.68; H, 8.82; N, 5.57. Found: C, 71.26; H, 8.70; N, 5.67.

EXAMPLE 6

4-(3'-Chlorophenyl)-α,α,1-trimethyl-4-piperidinemethanol 4-(3'-Chlorophenyl)-α,α,1-trimethyl-4-piperidinemethanol was prepared from 3-bromofluorobenzene using the procedure described in Example 2; m.p. 149°–150°; NMR (in CDCl$_3$): τ2.6–2.8 (m, 4H); 7.1–8.3 (m, 12H) and 8.8 (s, 6H). Anal. Calcd. for C$_{15}$H$_{22}$ClNO: C, 67.28; H, 8.28; N, 5.23. Found: C, 67.34; H, 8.15; N, 5.24.

EXAMPLE 7

4-(4'-Chlorophenyl)-α,α,1-trimethyl-4-piperidinemethanol 4-(4'-Chlorophenyl)-α,α,1-trimethyl-4-piperidinemethanol was prepared from 4-bromofluorobenzene using the procedure described in Example 2; m.p. 192°–194°. Anal. Calcd. for C$_{15}$H$_{22}$ClNO: C, 67.28; H, 8.28; N, 5.23. Found: C, 67.34; H, 8.13; N, 5.25.

EXAMPLE 8

4-(3'-Chlorophenyl)-α,α-diethyl-1-methyl-4-piperidinemethanol and its Hydrochloride 4-(3'-Chlorophenyl)-α,α-diethyl-1-methyl-4-piperidinemethanol was prepared from 3-bromochlorobenzene by the procedure described in Example 2 except that diethylketone (3-pentanone) was used in place of acetone in the preparation of III. The free base was converted to the hydrochloride which had a m.p. of 249°–250° (dec) after crystallization from ethanol; NMR (in CDCl$_3$): τ2.6 (m, 4H); 6.3–8.0 (m, 12H); 8.3–8.6 (quartet, 4H) and 9.2 (t, 6H). Anal. Calcd. for C$_{17}$H$_{27}$Cl$_2$NO: C, 61.44; H, 8.19; N, 4.21. Found: C, 61.19; H, 8.19; N, 4.19.

EXAMPLE 9

4-(2'-Tolyl)-α,α,1-trimethyl-4-piperidinemethanol 4-(2'-Tolyl)-α,α,1-trimethyl-4-piperidinemethanol was prepared from 2-bromotoluene by the procedure described in Example 2; m.p. 104°–105°; NMR (in CDCl$_3$): τ2.5–3.0 (m, 4H); 7.0–8.3 (m, 15H) and 8.9 (s, 6H). Anal. Calcd. for C$_{16}$H$_{25}$NO: C, 77.68; H, 10.19; N, 5.66. Found: C, 77.69; H, 10.19; N, 5.76.

EXAMPLE 10

4-(3'-Tolyl)-α,α,1-trimethyl-4-piperidinemethanol 4-(3'-Tolyl)-α,α,1-trimethyl-4-piperidinemethanol was prepared from 3-bromotoluene by the procedure described in Example 2; m.p. 139°–140°; NMR (in CDCl$_3$): τ2.6–3.1 (m, 4H); 7.2–8.5 (m, 15H) and 8.9 (s, 6H). Anal. Calcd. for C$_{16}$H$_{25}$NO: C, 77.68; H, 10.19; N, 5.66. Found: C, 77.68; H, 10.12; N, 5.83.

EXAMPLE 11

4-(4'-Tolyl)-α,α,1-trimethyl-4-piperidinemethanol 4-(4'-Tolyl)-α,α,1-trimethyl-4-piperidinemethanol was prepared from 4-bromotoluene by the procedure described in Example 2; m.p. 172°–174°; NMR (in CDCl$_3$): τ2.6–3.0 (m, 4H); 7.2–8.5 (m, 15H) and 8.9 (s, 6H). Anal. Calcd. for C$_{16}$H$_{25}$NO: C, 77.68; H, 10.19; N, 5.66. Found: C, 77.80; H, 10.23; N, 5.67.

EXAMPLE 12

4-(5'-m-Xylyl)-α,α,1-trimethyl-4-piperidinemethanol 4-(5'-m-Xylyl)-α,α,1-trimethyl-4-piperidinemethanol was prepared from 5-bromo-m-xylene by the procedure described in Example 2; m.p. 123°–125°; NMR (in CDCl$_3$): τ3.0–3.2 (m, 3H); 7.2–8.6 (m, 18H) and 8.9 (s, 6H). Anal. Calcd. for C$_{17}$H$_{27}$NO: C, 78.11; H, 10.41; N, 5.36. Found: C, 78.21; H, 10.19; N, 5.48.

EXAMPLE 13

4-(4'-o-Xylyl)-α,α,1-trimethyl-4-piperidinemethanol 4-(4'-o-Xylyl)-α,α,1-trimethyl-4-piperidinemethanol was prepared from 4-bromo-o-xylene by the procedure described in Example 2; m.p. 127°–128°; NMR (in CDCl$_3$): τ2.8–3.1 (m, 3H); 7.2–8.3 (m, 18H) and 8.9 (s, 6H). Anal. Calcd. for C$_{17}$H$_{27}$NO: C, 78.11; H, 10.41; N, 5.36. Found: C, 78.43; H, 10.11; N, 5.40.

EXAMPLE 14

4-(3'-Methoxyphenyl)-α,α-dimethyl-4-piperidinemethanol and its Hydrochloride

1-Benzyl-4-(3'-methoxyphenyl)-α,α-dimethyl-4-piperidinemethanol was prepared from 3-bromoanisole by the procedure described in Example 2 except that 1-benzyl-4-piperidone was used in place of 1-methyl-4-piperidone in the first step. This product (2.90 g) was dissolved in 20 mL of acetic acid, 0.49 g of 10% Pd/C was added, and the mixture was stirred under an atmosphere of hydrogen for 25 h. The mixture was filtered; the filtrate was concentrated, made basic, and extracted with methylene chloride to give 1.88 g of the crude free base (IV: R$^1$, R$^2$, R$^3$=H; R$^4$=m-MeOC$_6$H$_4$; R$^5$, R$^6$=Me). It was converted to the hydrochloride salt which had a m.p. of 232°–233° (dec) after crystallization from acetonitrile. NMR (in D$_2$O): τ2.6–3.3 (m, 4H); 6.3 (s, 3H); 6.6–8.3 (m, 9H) and 9.0 (s, 6H). Anal. Calcd. for C$_{15}$H$_{24}$ClNO$_2$: C, 63.04; H, 8.46; N, 4.90. Found: C, 63.19; H, 8.41; N, 4.87.

EXAMPLE 15

4-(2'-Methoxyphenyl)-α,α,1-trimethyl-4-piperidinemethanol 4-(2'-Methoxyphenyl)-α,α,1-trimethyl-4-piperidinemethanol was prepared from anisole by the procedure described in Example 3 except that acetone was used in place of cyclopentanone in the preparation of III; m.p. 110°–111°; NMR (in CDCl$_3$): τ2.6–3.1 (m, 4H); 6.2 (s, 3H); 6.7–8.5 (m, 9H); 7.9 (s, 3H) and 8.9 (broad s, 6H). Anal. Calcd. for C$_{16}$H$_{25}$NO$_2$: C, 72.96; H, 9.57; N, 5.32. Found: C, 73.02; H, 9.56; N, 5.41.

EXAMPLE 16

4-(3'-Methoxyphenyl)-α,α,1-trimethyl-4-piperidinemethanol 4-(3'-Methoxyphenyl)-α,α,1-trimethyl-4-piperidinemethanol was prepared from 3-bromoanisole by the procedure described in Example 2; m.p. 100°; NMR (in CDCl$_3$): τ2.6–3.3 (m, 4H); 6.1 (s, 3H); 7.1–8.3 (m, 12H); 8.9 (s, 6H). Anal. Calcd. for C$_{16}$H$_{25}$NO$_2$: C, 72.96; H, 9.57; N, 5.32. Found: C, 72.52; H, 9.42; N, 5.29.

EXAMPLE 17

4-(3'-Methoxyphenyl)-α,1-dimethyl-α-ethyl-4-piperidinemethanol 4-(3'-Methoxyphenyl)-α,1-dimethyl-α-ethyl-4-piperidinemethanol was prepared from 3-bromoanisole by the procedure described in Example 2 except that methyl ethyl ketone (2-butanone) was used in place of acetone in the preparation of III; m.p. 134°–135°; NMR (in CDCl$_3$): τ2.6–3.3 (m, 4H); 6.2 (s, 3H); 7.2–8.3 (m, 12H); 8.6 (quartet, 2H); 9.0 (s, 3H) and 9.2 (t, 3H). Anal. Calcd. for C$_{17}$H$_{27}$NO$_2$: C, 73.61; H, 9.81; N, 5.05. Found: C, 73.73; H, 9.69; N, 5.17.

EXAMPLE 18

4-(3'-Methoxyphenyl)-α,α-diethyl-1-methyl-4-piperidinemethanol and its Hydrochloride 4-(3'-Methoxyphenyl)-α,α-diethyl-1-methyl-4-piperidinemethanol was prepared from 3-bromoanisole by the procedure described in Example 2 except that diethyl ketone was used in place of acetone in the preparation of III. The product IV was converted to the hydrochloride which had a m.p. of 197°–198° (dec) after crystallization from isopropyl alcohol; NMR (in CDCl$_3$): τ2 (broad s, 1H); 2.5–3.2 (m, 4H); 6.1 (s, 3H); 6.3–8.6 (m, 16H); and 9.2 (t, 6H). Anal. Calcd. for C$_{18}$H$_{30}$ClNO$_2$: C, 65.93; H, 9.22; N, 4.27. Found: C, 65.91; H, 9.14; N, 4.72.

EXAMPLE 19

4-(4'-Methoxyphenyl)-α,α,1-trimethyl-4-piperidinemethanol 4-(4'-Methoxyphenyl)-α,α,1-trimethyl-4-piperidinemethanol was prepared from 4-bromoanisole by the procedure described in Example 2; m.p. 114°–115°; NMR (in CDCl$_3$): τ2.6–3.2 (m, 4H); 6.2 (s, 3H); 7.2–8.5 (m, 12H) and 8.9 (s, 6H). Anal. Calcd. for C$_{16}$H$_{25}$NO$_2$: C, 72.96; H, 9.57; N, 5.32. Found: C, 72.63; H, 9.47; N, 5.39.

EXAMPLE 20

4-(2',3'-Dimethoxyphenyl)-α,α,1-trimethyl-4-piperidinemethanol 4-(2',3'-Dimethoxyphenyl)-α,α,1-trimethyl-4-piperidinemethanol was prepared by the procedure described in Example 3 except that acetone was used in place of cyclopentanone in the preparation of III; m.p. 97°; NMR (in CDCl$_3$): τ2.9–3.3 (m, 3H); 6.2 (2s, 6H); 6.7–8.5 (12H) and 8.9 (broad, 6H). Anal. Calcd. for C$_{17}$H$_{27}$NO$_3$: C, 69.59; H, 9.28; N, 4.77. Found: C, 69.93; H, 9.17; N, 4.81.

EXAMPLE 21

4-(4'-Methylthiophenyl)-α,α,1-trimethyl-4-piperidinemethanol 4-(4'-Methylthiophenyl)-α,α,1-trimethyl-4-piperidinemethanol was prepared from 4-bromothioanisole by the procedure described in Example 2; m.p. 132°–133°; NMR (in CDCl$_3$): τ2.7 (s, 4H); 7.2–8.5 (m, +2s, 15H) and 8.9 (s, 6H). Anal. Calcd. for C$_{16}$H$_{25}$NOS: C, 68.77; H, 9.02; N, 5.01. Found: C, 68.82; H, 8.93; N, 5.12.

EXAMPLE 22

1-[1'-Methyl-4'-(3''-methoxyphenyl)-4'-piperidinyl]cyclobutanol

1-[1'-Methyl-4'-(3''-methoxyphenyl)-4'-piperidinyl]cyclobutanol was prepared from 3-bromoanisole by the procedure described in Example 2 except that cyclobutanone was used in place of acetone in the preparation of III; m.p. 105°; NMR (360 MHz in CDCl$_3$): τ 2.5 (t, 1H); 3.1 (d, split further, 1H); 3.1 (t, 1H); 3.2 (d/d, 1H); 6.2 (s, 3H); 7.8 (s, 3H) and 7.2–8.8 (m, 15H).

EXAMPLE 23

1-[1'-Methyl-4'-(2'',3''-dimethoxyphenyl)-4'-piperidinyl]cyclohexanol

1-[1'-Methyl-4'-(2'',3''-dimethoxyphenyl)-4'-piperidinyl]cyclohexanol was prepared by the procedure described in Example 3 except that cyclohexanone was used in place of cyclopentanone in the synthesis of III; m.p. 121°–123°; NMR (in CDCl$_3$): τ3.1 (t, 1H); 3.2 (m, 2H); 6.2 (2s, 6H); 7.0–7.3 (m, 4H); 7.7–9.1 (15H) and 7.9 (s, 3H). Anal. Calcd. for C$_{20}$H$_{31}$NO$_3$: C, 72.03; H, 9.37; N, 4.20. Found: C, 71.58; H, 9.22; N, 4.48.

EXAMPLE 24

4-(1'-Methyl-2'-pyrrolyl)-α,α,1-trimethyl-4-piperidinemethanol 4-(1'-Methyl-2'-pyrrolyl)-α,α,1-trimethyl-4-piperidinemethanol was prepared by the procedure described in Example 3 except that 1-methylpyrrole was used in place of veratrole in the preparation of I and acetone was used in place of cyclopentanone in the preparation of III; m.p. 110°–111°; NMR (in CDCl$_3$): τ3.5 (m, 1H); 4.0 (m, 2H); 6.2 (s, 3H); 7.1–8.5 (m, 12H) and 8.8 (s, 6H).

EXAMPLE 25

4-(5'-Methyl-2'-thienyl)-α,α,1-trimethyl-4-piperidinemethanol 4-(5'-Methyl-2'-thienyl)-α,α,1-trimethyl-4-piperidinemethanol was prepared by the procedure described in Example 3 except that 2-methylthiophene was used in place of veratrole in the preparation of I and acetone was used in place of cyclopentanone in the preparation of III; m.p. 113°–114°; NMR (360 MHz in CDCl$_3$): τ3.35 (AB quartet, J=3.5 Hz, lower-field compound split into quartets, J=0.7 Hz; 2H); 7.3 (m, 2H); 7.5 (d, J=0.7 Hz, 3H); 7.8 (s, 3H); 8.0 (m, 6H); 8.4 (broad s, 1H) and 8.8 (s, 6H).

EXAMPLE 26

4-(3'-Pyridyl)-α,α,1-trimethyl-4-piperidinemethanol 4-(3'-Pyridyl)-α,α,1-trimethyl-4-piperidinemethanol was prepared from 3-bromopyridine by the procedure described in Example 2 except that the dehydration of the carbinol I was carried out by heating with trifluoroacetic acid to 180° instead of under reflux; m.p. 131°–133°; NMR (360 MHz in CDCl$_3$): τ1.4 (d, J=2.5 Hz, 1H); 1.5 (d/d, J=4.5/1.5 Hz, 1H); 2.3 (d/t, J=8.5/2 Hz, 1H); 2.7 (d/d, J=8.5/4.5 Hz, 1H); 7.2 (d, split further, 2H); 7.6 (d, 2H); 7.8–7.9 (m+s, 5H); 8.1 (broad s, 1H) and 8.8 (s, 6H).

EXAMPLE 27

1-[1'-Methyl-4'-(3''-methoxyphenyl)-4'-piperidinyl]cycloheptanol

1-[1'-Methyl-4'-(3''-methoxyphenyl)-4'-piperidinyl]-cycloheptanol was prepared from 3-bromoanisole by the procedure described in Example 2 except that cycloheptanone was used in place of acetone in the preparation of III; m.p. 139°–140°; NMR (in CDCl$_3$): τ 2.6–3.3 (m, 4H); 6.2 (s, 3H) and 7.2–9.0 (m+s, 24H). Anal. Calcd. for $C_{20}H_{31}NO_2$: C, 75.67; H, 9.84; N, 4.41. Found: C, 76.23; H, 9.64; N, 4.28.

EXAMPLE 28

1-[1'-Methyl-4'-(3''-methoxyphenyl)-4'-piperidinyl]cyclooctanol

1-[1'-Methyl-4'-(3''-methoxyphenyl)-4'-piperidinyl]-cyclooctanol was prepared from 3-bromoanisole by the procedure described in Example 2 except that cyclooctanone was used in place of acetone in the preparation of III; m.p. 120°–122°; NMR (in CDCl$_3$): τ 2.6–3.3 (m, 4H); 6.2 (s, 3H) and 7.2–9.0 (m+s, 26H). Anal. Calcd. for $C_{21}H_{33}NO_2$: C, 76.09; H, 10.03; N, 4.33. Found: C, 76.11; H, 9.70; N, 4.09.

EXAMPLE 29

4-(2',5'-Dimethoxyphenyl)-α,α,1-trimethyl-4-piperidinemethanol 4-(2',5'-Dimethoxyphenyl)-α,α,1-trimethyl-4-piperidinemethanol was prepared from 1,4-dimethoxybenzene by the procedure described in Example 3 except that acetone was used in place of cyclopentanone in the synthesis of III; m.p. 139°–140°; NMR (in CDCl$_3$): τ 3.0–3.3 (m, 3H); 6.2 (2s, 6H); 6.6–8.5 (m+s, 12H) and 8.9 (broad, 6H). Anal. Calcd. for $C_{17}H_{27}NO_3$: C, 69.59; H, 9.29; N, 4.77. Found: C, 69.66; H, 9.09; N, 4.66.

EXAMPLE 30

1-[1'-Methyl-4'-(3''-trifluoromethylphenyl)-4'-piperidinyl]cyclopentanol

1-[1'-Methyl-4'-(3''-trifluoromethylphenyl)-4'-piperidinyl]cyclopentanol was prepared by the procedure described in Example 2 except that cyclopentanone was used in place of acetone in the preparation of III; m.p. 137°–138°. Anal. Calcd. for $C_{18}H_{24}F_3NO$: C, 66.04; H, 7.34; N, 4.09. Found: C, 66.14; H, 7.23; N, 4.09.

EXAMPLE 31

4-(3'-Trifluoromethylphenyl)-α,1-dimethyl-α-ethyl-4-piperidinemethanol and its Hydrochloride 4-(3'-Trifluoromethylphenyl)-α,1-dimethyl-α-ethyl-4-piperidinemethanol was prepared by the procedure described in Example 2 except that methyl ethyl ketone was used in place of acetone in the preparation of III. The product IV was converted to the hydrochloride salt which had a m.p. of 227°–228° (dec); NMR (360 MHz in CDCl$_3$): τ 2.4–2.5 (m, 4H); 6.5 (m, 2H); 7.0–7.6 (m, 10H); 8.5 (m, 1H); 8.8 (m, 1H); 8.9 (s, 3H) and 9.1 (t, 3H).

EXAMPLE 32

4-(4'-Phenoxyphenyl)-α,α,1-trimethyl-4-piperidinemethanol 4-(4'-Phenoxyphenyl)-α,α,1-trimethyl-4-piperidinemethanol was prepared from p-bromophenyl phenyl ether by the procedure described in Example 2; m.p. 148°. Anal. Calcd. for $C_{21}H_{27}NO_2$: C, 77.50; H, 8.36; N, 4.30. Found: C, 77.25; H, 8.13; N, 4.33.

EXAMPLE 33

4-(4'-Dimethylaminophenyl)-α,α,1-trimethyl-4-piperidinemethanol 4-(4'-Dimethylaminophenyl)-α,α,1-trimethyl-4-piperidinemethanol was prepared from p-bromo-N,N-dimethylaniline by the procedure described in Example 2 except that the dehydration of the carbinol was carried out by heating with trifluoroacetic acid in a sealed tube to 140° for 4 h instead of under reflux; m.p. 142°–143°. Anal. Calcd. for $C_{17}H_{28}N_2O$: C, 73.87; H, 10.21; N, 10.13. Found: C, 73.89; H, 10.15; N, 10.27.

EXAMPLE 34

1[1'-Methyl-4'-(3''-methoxyphenyl)-4'-piperidine]cyclopentanol

1[1'-Methyl-4'-(3''-methoxyphenyl)-4'-piperidine]cyclopentanol was prepared from m-bromoanisole by the procedure described in Example 2 except that cyclopentanone was used in place of acetone in the preparation of III; m.p. 108°–109°. Anal. Calcd. for $C_{18}H_{27}NO_2$: C, 74.70; H, 9.40; N, 4.84. Found: C, 74.99; H, 9.12; N, 5.03.

EXAMPLE 35

1[1'-Methyl-4'-(3''-methoxyphenyl)-4'-piperidine]cyclohexanol

1[1'-Methyl-4'-(3''-methoxyphenyl)-4'-piperidine]cyclohexanol was prepared from m-bromoanisole by the procedure described in Example 2 except that cyclohexanone was used in place of acetone in the preparation of III. The product IV was converted to the hydrochloride salt which had a m.p. of 255° (dec); NMR (in CDCl$_3$): τ 2.5–2.8 (m, 1H); 3.0–3.3 (m, 2H); 6.2 (s, 3H) and 6.4–9.3 (m, 22H).

EXAMPLE 36

4-(3'-Biphenylyl)-α,α,1-trimethyl-4-piperidinemethanol and its Hydrochloride 4-(3'-Biphenylyl)-α,α,1-trimethyl-4-piperidinemethanol was prepared from 3-bromobiphenyl by the procedure described in Example 2. The product IV was converted to the hydrochloride salt which had a m.p. of 221°–223° (dec); NMR (in CDCl$_3$): τ 2.2–2.7 (m, 9H); 6.3–7.7 (m, 12H) and 8.7 (s, 6H).

EXAMPLE 37

4-(2',3'-Dimethoxyphenyl)-1-benzyl-α,α-dimethyl-4-piperidinemethanol and its Hydrochloride 4-(2',3'-Dimethoxyphenyl)-1-benzyl-α,α-dimethyl-4-piperidinemethanol was prepared by the procedure described in Example 3 except that 1-benzyl-4-piperidone was used in place of 1-methyl-4-piperidone in the preparation of I and acetone was used in place of cyclopentanone in the preparation of III. The product IV was converted to the hydrochloride salt which had a m.p. of 236°–237° (dec) after crystallization from acetonitrile. Anal. Calcd. for $C_{23}H_{32}ClNO_3$: C, 68.05; H, 7.95; N, 3.45. Found: C, 68.37; H, 7.80; N, 3.69.

EXAMPLE 38

1-[1'-Benzyl-4'-(2",3"-dimethoxyphenyl)-4'-piperidinyl]cyclopentanol and its Hydrochloride 1-[1'-Benzyl-4'-(2",3"-dimethoxyphenyl)-4'-piperidinyl]cyclopentanol was prepared by the procedure described in Example 3 except that 1-benzyl-4-piperidone was used in place of 1-methyl-4-piperidone in the first step. The product IV was converted to the hydrochloride salt which had a m.p. of 235° (dec) after crystallization from 90% ethanol. Anal. Calcd. for $C_{25}H_{34}ClNO_3$: C, 69.51; H, 7.93; N, 3.24. Found: C, 69.29; H, 7.71; N, 3.59.

EXAMPLE 39

4-(6'-Methoxy-2'-naphthyl)-α,α,1-trimethyl-4-piperidinemethanol 4-(6'-Methoxy-2'-naphthyl)-α,α,1-trimethyl-4-piperidinemethanol was prepared from 2-bromo-6-methoxynaphthalene by the procedure described in Example 2; m.p. 170°-171°. Anal. Calcd. for $C_{20}H_{27}NO_2$: C, 76.64; H, 8.68; N, 4.47. Found: C, 76.59; H, 8.73; N, 4.38.

EXAMPLE 40

4-(3'-Ethoxyphenyl)-α,α,1-trimethyl-4-piperidinemethanol and its Hydrochloride 4-(3'-Ethoxyphenyl)-α,α,1-trimethyl-4-piperidinemethanol was prepared from 3-ethoxybromobenzene by the procedure described in Example 2; the free base was converted to the hydrochloride salt which had a m.p. of 229°-230° after crystallization from isopropyl alcohol. Anal. Calcd. for $C_{17}H_{28}ClNO_2$: C, 65.05; H, 8.99; N, 4.46. Found: C, 65.19; H, 9.03; N, 4.64.

EXAMPLE 41

4-(3'-Trifluoromethylphenyl)-α,α-dimethyl-1-ethyl-4-piperidinemethanol 4-(3'-Trifluoromethylphenyl)-α,α-dimethyl-1-ethyl-4-piperidinemethanol was prepared as described in Example 2 except that 1-ethyl-4-piperidone was used in place of 1-methyl-4-piperidone in the first step; m.p. 110°. Anal. Calcd. for $C_{17}H_{24}F_3NO$: C, 64.74; H, 7.67; N, 4.44. Found: C, 64.73; H, 7.90; N, 4.55.

EXAMPLE 42

4-(4'-Biphenylyl)-α,α,1-trimethyl-4-piperidinemethanol 4-(4'-Biphenylyl)-α,α,1-trimethyl-4-piperidinemethanol was prepared from 4-bromobiphenyl by the procedure described in Example 2; m.p. 192°-193°; NMR (in CDCl₃): τ2.2-2.8 (m, 9H); 7.1-8.5 (m+s, 12H) and 8.8 (s, 6H).

EXAMPLE 43

4-(3'-Methoxyphenyl)-α,α,1,3-tetramethyl-4-piperidinemethanol 4-(3'-Methoxyphenyl)-α,α,1,3-tetramethyl-4-piperidinemethanol was prepared from 3-bromoanisole by the procedure of Example 2 except that 1,3-dimethyl-4-piperidone was used in place of 1-methyl-4-piperidone in the preparation of II. The product was obtained as an oil, distilling at a bath temperature of 130°-160° under $5 \times 10^{-4}$ Torr (0.07 Pa) vacuum; it was a mixture (ratio 83/17) of two isomers ($R^3$ cis or trans to the aryl group) as determined by 360 MHz NMR spectroscopy. The major isomer has the C-3 methyl group as a doublet (J=7.2 Hz) at τ 8.5 and the two α-methyl groups at 8.7 and 8.9. MS Calcd. for $C_{17}H_{27}NO_2$: m/z 277.204. Found: 277.204.

EXAMPLE 44

4-(3'-Tolyl)-α,α,1,2-tetramethyl-4-piperidinemethanol 4-(3'-Tolyl)-α,α,1,2-tetramethyl-4-piperidinemethanol was prepared from 3-bromotoluene by the procedure of Example 2 except that 1,2-dimethyl-4-piperidone was used in place of 1-methyl-4-piperidone in the preparation of II; m.p. 139°; NMR (360 MHz in CDCl₃): τ 2.8-2.9 (m, 3H); 3.0 (d, split further, 1H); 7.0 (m, 1H); 7.4 (m, 2H); 7.5-7.9 (m+2s, 10H); 8.0 (broad s, 1H); 8.9 (two s, 6H) and 9.4 (d, J=7 Hz, 3H). Anal. Calcd. for $C_{17}H_{27}NO$: C, 78.11; H, 10.41; N, 5.36. Found: C, 78.23; H, 10.31; N, 5.30.

EXAMPLE 45

7-(3'-Trifluoromethylphenyl)-α,α-dimethyl-7-indolizidinemethanol 7-(3'-Trifluoromethylphenyl)-α,α-dimethylindolizidinemethanol was prepared by the procedure of Example 2 except that 7-indolizidinone was used in place of 1-methyl-4-piperidone in the preparation of II. The product was a mixture of two stereoisomers in the ratio of 3:2, m.p. 120°-122°. Anal. Calcd. for $C_{18}H_{24}F_3NO$: C, 66.04; H, 7.39; N, 4.28. Found: C, 65.99; H, 7.48; N, 4.39.

EXAMPLE 46

(±)-cis and trans-3-Methyl-1-[1'-methyl-4'-(3"-trifluoromethylphenyl)-4'-piperidinyl]cyclopentanol (±)-cis and trans-3-Methyl-1-[1'-methyl-4'-(3"-trifluoromethylphenyl)-4'-piperidinyl]cyclopentanol was prepared, as a 60/40 mixture of the two racemic diastereomers, by the procedure described in Example 2 except that (±)-3-methylcyclopentanone was used in place of acetone in the preparation of III; m.p. 112°-113°. ¹⁹F NMR spectrum; singlet at −62.6 ppm (from Freon®11 CFCl₃); ¹H-NMR spectrum: two doublets (J=7 Hz) at 9.0 and 9.1 in the ratio of 2:3, among others.

EXAMPLE 47

(−)-cis and trans-3-Methyl-1-[1'-methyl-4'-(3"-trifluoromethylphenyl)-4'-piperidinyl]cyclopentanol (−)-cis and trans-3-Methyl-1-[1'-methyl-4'-(3"-trifluoromethylphenyl)-4'-piperidinyl]cyclopentanol was prepared, as a mixture of two optically active diastereomers, by the procedure described in Example 2 except that (−)-3-methylcyclopentanone was used in the preparation of III; m.p. 103°-104°. $[α]_D$ −6.7° (c=1.07, CHCl₃). The NMR spectra were identical to those of the product of Example 46.

DOSAGE FORMS

The antidepressant agents of this invention can be administered as treatment for psychiatric depressions of the reactive and endogenous types by any means that produces contact of the active agent with the agent's site of action in the body of a mammal. They can be administered by any conventional means available for use in conjunction with pharmaceuticals, either as individual therapeutic agents or in a combination of therapeutic agents. They can be administered alone, but are generally administered with a pharmaceutical carrier selected on the basis of the chosen route of administration and standard pharmaceutical practice.

The dosage administered will, of course, vary depending upon known factors, such as the pharmacodynamic characteristics of the particular agent and its mode and route of administration; the age, health and weight of the recipient; the nature and extent of the symptoms; the kind of concurrent treatment; the frequency of treatment; and the effect desired. Usually, a daily dosage of active ingredient can be about 0.001 to 50 milligrams per kilogram of body weight. Ordinarily, a total of 0.01 to 20, preferably 0.1 to 10, milligrams per day per kilogram of body weight, given in divided doses 2 to 4 times a day or in sustained release form, is effective to obtain the desired therapeutic results.

Dosage forms (compositions) suitable for internal administration can contain about 0.25 to about 10 milligrams of active ingredient per unit. In such pharmaceutical compositions the active ingredient will ordinarily be present in an amount of about 0.01–90% by weight, based on the total weight of the composition.

The active ingredient can be administered orally in solid dosage forms, such as capsules, tablets and powders, or in liquid dosage forms, such as elixirs, syrups and suspensions; it can also be administered parenterally, in sterile liquid dosage forms, or rectally in the form of suppositories.

Gelatin capsules can contain the active ingredient and powdered carriers, such as lactose, sucrose, mannitol, starch, cellulose derivatives, magnesium stearate and stearic acid. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or they can be enteric coated for selective disintegration in the gastrointestinal tract.

Liquid dosage forms for oral administration can contain coloring and flavoring to increase patient acceptance.

In general, water, a suitable oil, saline, aqueous dextrose (glucose) and related sugar solutions and glycols, such as propylene glycol or the polyethylene glycols, are suitable carriers for parenteral solutions. Solutions for parenteral administration contain preferably a water-soluble salt of the active ingredient, suitable stabilizing agents and, if necessary, buffer substances. Antioxidizing agents, such as sodium bisulfite, sodium sulfite and ascorbic acid, either alone or combined, are suitable stabilizing agents. Also used are citric acid and its salts and sodium EDTA (ethylenediaminetetraacetic acid). In addition, parenteral solutions can contain preservatives, such as benzalkonium chloride, methyl- or propylparaben and chlorobutanol.

Suppositories can contain the active ingredient in a suitable oleaginous or water-soluble base. The oleaginous class includes cocoa butter and other fats with similar properties; the water-soluble class includes the polyethylene glycols.

Suitable pharmaceutical carriers are described by E. W. Martin in *Remington's Pharmaceutical Sciences*, a standard reference text in this field.

Useful pharmaceutical dosage forms for administration of the compounds of this invention are illustrated below.

CAPSULES (HARD)

Hard capsules can be prepared by filling standard two-piece hard gelatin capsules with the following mixture using conventional encapsulating equipment:
Active ingredient: 1 mg
Lactose: 125 mg
Talc: 12 mg
Magnesium stearate: 3 mg

CAPSULES (Soft)

A mixture of active ingredient in soybean oil can be prepared and injected by means of a positive displacement pump in gelatin to form soft gelatin capsules containing 5 mg of the active ingredient. The capsules can be washed in petroleum ether and dried.

TABLETS

Tablets can be prepared by conventional procedures so that each unit will contain:
Active ingredient: 1 mg
Spray dried lactose: 150 mg
Microcrystalline cellulose: 35 mg
Magnesium stearate: 3 mg

PARENTERAL

Parenteral composition suitable for intramuscular administration can be prepared so that each mL contains, percentages being by weight:
Active ingredient: 1 mg
Sodium carboxymethyl cellulose: 0.75%
Polysorbate 80: 0.04%
Benzyl alcohol: 0.9%
Sodium chloride: 0.9%
Water for injection Q.S.: 1 mL

SUSPENSION

An aqueous suspension can be prepared for oral administration so that each 5 mL contain, percentages being by weight:
Active ingredient: 5 mg
Methylcellulose: 5%
Carboxymethyl cellulose: 5%
Syrup: 30%
Polysorbate 80: 0.2%
Sodium saccharin: 2 mg
Cherry flavor: 0.1%
Sodium benzoate: 5 mg
Water Q.S.: 5 mL

USE

A standard procedure for detecting and comparing the antidepressant activity of the compounds of this invention, for which there is good correlation with human efficacy, is the prevention of tetrabenazine-induced sedation and depression in mice. (Everett, "The Dopa Response Potentiation Test and Its Use in Screening for Antidepressant Drugs", pp. 164–167 in *Antidepressant Drugs* [Proceedings of the First International Symposium], S. Garattini and M. N. G. Dukes (editors), 1967).

Groups of 10 Carworth $CF_1S$ female mice, 18–21 g each, each fasted 1.5 h and were intubated with antagonist compounds at oral doses, such as 0, 1, 3, 9, 27 and 81 mg/kg in 0.20 mL of 1% Methocel ® (methylcellulose). The mice were challenged 30 minutes later with tetrabenazine (as the methanesulfonate), 32 mg/kg intraperitoneally (dissolved in 0.20 mL 0.05% aqueous KCl at pH 2.0). One hour after administration of antagonist (30 minutes after administration of tetrabenazine) the mice were examined for signs of exploratory activity and ptosis (eye lid closure). Normal exploratory activity (relief from sedation) was recorded when a mouse, lifted by the tail from a group of 10 in a testing box and placed on a stainless steel testing box lid (12.5 inch (31.8 cm) by 8 inch (20.3 cm) with 0.33 inch mesh), either turned its head horizontally 30° in both directions or moved to the edge of the screen within 10 seconds after being placed on the screen. Relief from ptosis was recorded when, at exactly two seconds after placing the mouse facing the observer, lid closure was less than 50% in both eyes. The following table shows the data obtained from testing compounds of the aforesaid examples.

TABLE 2

ANTAGONISM OF TETRABENAZINE-INDUCED DEPRESSION IN MICE ORALLY AT ONE HOUR POST-DRUG

| EXAMPLE | ORAL $ED_{50}$ (mg/kg) FOR PREVENTION OF | |
|---|---|---|
| | EXPLORATORY LOSS | PTOSIS |
| 1 | | 5.6 | 0.78 |
| 2 | | 0.01 | 0.016 |
| 2A | | 0.01 | 0.014 |
| 3 | | 14. | 2.8 |
| 4 | | 0.20 | 0.12 |
| 5 | | 0.48 | 0.33 |
| 6 | | 0.04 | 0.03 |
| 7 | | 0.57 | 0.33 |
| 8 | (HCl Salt) | 0.29 | 0.26 |
| 9 | | 0.48 | 0.33 |
| 10 | | 0.04 | 0.04 |
| 11 | | 0.69 | 0.57 |
| 12 | | 0.11 | 0.064 |
| 13 | | 0.30 | 0.23 |
| 14 | (HCl Salt) | 4.4 | 2.7 |
| 15 | | 2.3 | 0.57 |
| 16 | | 0.12* | 0.077* |
| 17 | | 0.10 | 0.11 |
| 18 | (HCl Salt) | 0.71 | 0.71 |
| 19 | | 1.1 | 0.33 |
| 20 | | 4.6 | 2.1 |
| 21 | | 1.3 | 1.3 |
| 22 | | 0.92 | 0.67 |
| 23 | | 38. | 17. |
| 24 | | 1.2 | 0.78 |
| 25 | | 0.99 | 0.69 |
| 26 | | 29. | 18. |
| 27 | | 1.4 | 0.9 |
| 28 | | 3.8 | 1.7 |
| 29 | | 0.99 | 0.86 |
| 30 | | 0.17 | 0.084 |
| 31 | (HCl Salt) | 0.064 | 0.056 |
| 32 | | >81 | 81 |
| 33 | | 0.78 | 0.35 |
| 34 | | 0.48 | 0.45 |
| 35 | | 1.4 | 1.1 |
| 36 | (HCl Salt) | 1.1 | 0.66 |
| 37 | (HCl Salt) | >81 | 81 |
| 38 | (HCl Salt) | >81 | >81 |
| 39 | | 0.33 | <0.33 |
| 40 | (HCl Salt) | 0.9 | 0.9 |
| 41 | | 0.73 | 0.46 |
| 42 | | 1.5 | 1.0 |
| 43 | | 7.2 | 5.8 |
| 44 | | 0.33 | 0.33 |
| 45 | | <0.33 | 0.48 |
| 46 | | <1 | <1 |
| 47 | | <1 | <1 |
| Amtriptyline (Standard) | | 2.7 | 0.7 |
| Imipramine (Standard) | | 2.2 | 0.94 |

TABLE 2-continued

ANTAGONISM OF TETRABENAZINE-INDUCED DEPRESSION IN MICE ORALLY AT ONE HOUR POST-DRUG

| EXAMPLE | ORAL $ED_{50}$ (mg/kg) FOR PREVENTION OF | |
|---|---|---|
| | EXPLORATORY LOSS | PTOSIS |

*peak time values

PROTOCOL FOR ANOREXIA DATA FROM CNS SCREEN

Female mice weighing 16-20 grams and fasted overnight for 17-21 h are used in these studies. At 0.5 h after administration of graded oral doses of compound prepared in aqueous Methocel ® (methylcellulose, viscosity 100 CPS, grade MC, Dow Chemical Co.) and 2.8% Tween 80 and dosed at 0.1 mL per 10 grams of body weight, each mouse is transferred to an individual, clear, Lucite ® compartment (13.3 cm × 12.7 cm × 12.7 cm) with a 0.64 cm × 0.64 cm wire mesh floor. Five compartments are linearly arranged in each cage unit. Inside each compartment is a section of a black Lucite ® bar (13 cm × 1.2 cm × 1.2 cm), in the top of which are ten spot depressions (0.8 cm diameter), each containing 0.05 mL of 50% sweetened condensed milk (Borden's Eagle Brand). 30 Minutes later the mice are returned to the "shoe-box" containers and the number of milk spots consumed by each mouse is counted. Fractions of spots consumed are also estimated and counted. Five mice mg per drug dose can drink a maximum of 50 spots (2.5 mL of milk). Nine or fewer spots consumed by 5 mice is considered to indicate anorexia. $ED_{50}$ values are estimated based on the quantal responses obtained.

The data tabulated in Table 3 show that certain compounds of this invention have utility as anorectic agents, and thus may be useful in treating obesity.

TABLE 3

| EXAMPLE | $ED_{50}$ FOR ANOREXIA |
|---|---|
| 2 | 60 mg/kg |
| 2A | 36 |
| 4 | 60 |
| 6 | 60 |
| 7 | 20 |
| 8 | 20 |
| 10 | 20 |
| 16 | 60 |
| 17 | 60 |
| 30 | 60 |
| 31 | 20 |
| 32 | 60 |
| 37 | 60 |
| 39 | 60 |
| 41 | 60 |

BEST MODE FOR CARRYING OUT THE INVENTION

The best mode presently contemplated for carrying out the invention is represented by the antidepressant of Example 2.

INDUSTRIAL APPLICABILITY

As is apparent from the description provided herein, the antidepressants and anorectic agents of this invention are useful in the field of medicine, particularly in the areas of mental disorders and obesity.

Although the preferred embodiments of the invention have been illustrated and described above, it is to be understood that it is not intended to limit the invention to the precise constructions disclosed herein and it is to be further understood that the right is reserved to all changes and modifications coming within the scope of the invention as defined in the appended claims.

We claim:

1. 4-Aryl-4-piperidinecarbinol of the formula:

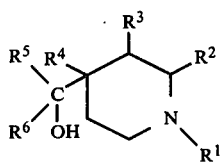

wherein
(a) $R^1$ is H, alkyl of 1 to 12 carbon atoms, cycloalkyl of 3 to 8 carbon atoms or benzyl;
(b) each of $R^2$ and $R^3$ is independently selected from H and lower alkyl of 1 to 4 carbon atoms; $R^1$ and $R^2$ taken together is a branched or unbranched alkylene bridge wherein the bridge is of 3 or 4 carbon atoms; or $R^2$ and $R^3$ taken together is a branched or unbranched alkylene bridge wherein the bridge is of 3 to 6 carbon atoms;
(c) $R^4$ is
 (1) phenyl or 2-naphthyl or phenyl or 2-naphthyl substituted with one or two substituents, the same or different, selected from F, Cl, alkyl, perfluoroalkyl, alkoxy, aryloxy, alkylthio, arylthio, perfluoroalkoxy, perfluoroalkylthio and dialkylamino, said alkyl and alkoxy moieties being of 1 to 12 carbon atoms and said aryl moieties being of 6 to 12 carbon atoms;
 (2) 2-, 3-, or 4-biphenylyl or 2-, 3-, or 4-biphenylyl wherein either or both aromatic moieties is substituted with one or two substituents, the same or different, selected from F, Cl, alkyl, perfluoroalkyl, alkoxy, aryloxy, alkylthio, arylthio, perfluoroalkoxy, perfluoroalkylthio and dialkylamino, said alkyl and alkoxy moieties being of 1 to 12 carbon atoms and said aryl moieties being of 6 to 12 carbon atoms;
 (3) 2-pyrrolyl or 2-pyrrolyl substituted with one to three lower alkyl groups of 1 to 4 carbon atoms;
 (4) 2-, 3-, or 4-pyridyl; or
 (5) 2-thienyl substituted in the 5-position with lower alkyl of 1 to 4 carbon atoms; and
(d) each of $R^5$ and $R^6$ is independently selected from alkyl of 1 to 12 carbon atoms and cycloalkyl of 3 to 8 carbon atoms or $R^5$ and $R^6$ taken together is a branched or unbranched alkylene bridge wherein the bridge is of 3 to 11 carbon atoms,
provided, however, when $R^1$, $R^5$ and $R^6$ are methyl and $R^2$ and $R^3$ are H, then $R^4$ is not p-t-butylphenyl or 2'-biphenylyl.

2. 4-Aryl-4-piperidinecarbinol of claim 1 wherein $R^1$, $R^5$ and $R^6$ are methyl, $R^2$ and $R^3$ are H and $R^4$ is m—$CF_3C_6H_4$.

3. Hydrochloride of the 4-aryl-4-piperidinecarbinol of claim 2.

4. 4-Aryl-4-piperidinecarbinol of claim 1 wherein $R^4$ is phenyl which is m-substituted.

5. 4-Aryl-4-piperidinecarbinol of claim 1 wherein $R^1$ is benzyl.

6. Pharmaceutical composition containing a pharmaceutically effective antidepressive amount of the 4-aryl-4-piperidinecarbinol of claim 1.

7. Pharmaceutical composition containing a pharmaceutically effective antidepressive amount of the 4-aryl-4-piperidinecarbinol of claim 2.

8. Pharmaceutical composition containing a pharmaceutically effective antidepressive amount of the hydrochloride of claim 3.

9. Pharmaceutical composition containing a pharmaceutically effective antidepressive amount of the 4-aryl-4-piperidinecarbinol of claim 4.

10. Pharmaceutical composition containing a pharmaceutically effective antidepressive amount of the 4-aryl-4-piperidinecarbinol of claim 5.

11. Method for treating depression, which method comprises administering a pharmaceutically effective antidepressive amount of the 4-aryl-4-piperidinecarbinol of claim 1.

12. Method for treating depression, which method comprises administering a pharmaceutically effective antidepressive amount of the 4-aryl-4-piperidinecarbinol of claim 2.

13. Method for treating depression, which method comprises administering a pharmaceutically effective antidepressive amount of the hydrochloride of claim 3.

14. Method for treating depression, which method comprises administering a pharmaceutically effective antidepressive amount of the 4-aryl-4-piperidinecarbinol of claim 4.

15. Method for treating depression, which method comprises administering a pharmaceutically effective antidepressive amount of the 4-aryl-4-piperidinecarbinol of claim 5.

* * * * *